(12) United States Patent
Song et al.

(10) Patent No.: US 11,426,157 B2
(45) Date of Patent: Aug. 30, 2022

(54) METHOD OF PREPARING SUTURE ANCHOR USING SUTURE AND PREPARED SUTURE ANCHOR

(71) Applicant: AJU PHARM CO., LTD., Seoul (KR)

(72) Inventors: Jae Young Song, Seoul (KR); Jin Kwon Lee, Seoul (KR)

(73) Assignee: AJU PHARM CO., LTD., Seoul (KR)

( * ) Notice: Subject to any disclaimer, the term of this patent is extended or adjusted under 35 U.S.C. 154(b) by 231 days.

(21) Appl. No.: 16/481,565

(22) PCT Filed: Apr. 27, 2019

(86) PCT No.: PCT/KR2019/005111
§ 371 (c)(1),
(2) Date: Jul. 29, 2019

(87) PCT Pub. No.: WO2019/231114
PCT Pub. Date: Dec. 5, 2019

(65) Prior Publication Data
US 2020/0237364 A1    Jul. 30, 2020

(30) Foreign Application Priority Data
May 30, 2018 (KR) ........................ 10-2018-0061558

(51) Int. Cl.
*A61B 17/04* (2006.01)
*A61B 17/06* (2006.01)
(52) U.S. Cl.
CPC .... *A61B 17/0491* (2013.01); *A61B 17/06195* (2013.01)

(58) Field of Classification Search
CPC ............ A61B 17/0401; A61B 17/0491; A61B 17/06166; A61B 2017/06171;
(Continued)

(56) References Cited

U.S. PATENT DOCUMENTS 6,517,564 B1     2/2003  Grafton et al.
9,173,645 B2 *  11/2015  Overes ............... A61B 17/0487
(Continued)

FOREIGN PATENT DOCUMENTS

JP     2011-194238 A    10/2011
JP     2018-509255 A     4/2018
(Continued)

*Primary Examiner* — Tan-Uyen T Ho
*Assistant Examiner* — Bridget E. Rabaglia
(74) *Attorney, Agent, or Firm* — IP Legal Services, LLC

(57) ABSTRACT

The present invention relates to a method of preparing a suture anchor using a suture and a prepared suture anchor. A knitting member (100) cut at a predetermined width and length while having a plurality of knots (10*a*) is inserted into a hole 1*a* of a bone 1 using an anchor inserting device 200, and a second suture 20 provided between one knot 10*a* of the plurality of knots and another knot 10*a* thereof is pulled rearwards, and thus the knitting member (100) is deformed from a long rod shape to a lump shape the bone 1. Accordingly, the knitting member (100) has a volume larger than a diameter of the hole 1*a*, and the knitting member (100) deformed into the lump shape is configured not to be removed from the hole 1*a* of the bone 1 even when the second suture 20 is further pulled in a rear direction.

3 Claims, 12 Drawing Sheets

(58) Field of Classification Search
CPC .. A61B 2017/06176; A61B 2017/0406; A61B 17/04; A61B 2017/0417; A61B 2017/0419; A61B 2017/0427; A61B 2017/0429; A61B 2017/0433; A61B 2017/0432; A61B 2017/0438; A61B 2017/0445; A61B 2017/0446; A61B 2017/0464; A61B 2017/0462; A61B 17/0466; A61B 17/06195; A61F 2002/0817
USPC ................ 606/144, 139, 230, 228, 232, 233
See application file for complete search history.

(56) References Cited

U.S. PATENT DOCUMENTS

| | | |
|---|---|---|
| 2002/0087190 A1 | 7/2002 | Benavitz et al. |
| 2004/0098045 A1 | 5/2004 | Grafton et al. |
| 2005/0222618 A1 | 10/2005 | Dreyfuss et al. |
| 2006/0161159 A1 | 7/2006 | Dreyfuss et al. |
| 2007/0060922 A1 | 3/2007 | Dreyfuss |
| 2007/0073299 A1 | 3/2007 | Dreyfuss et al. |
| 2007/0150003 A1 | 6/2007 | Dreyfuss et al. |
| 2007/0225764 A1 | 9/2007 | Benavitz et al. |
| 2007/0288027 A1 | 12/2007 | Grafton et al. |
| 2010/0094337 A1 | 4/2010 | Maiorino |
| 2010/0191284 A1 | 7/2010 | Dreyfuss et al. |
| 2010/0204730 A1 | 8/2010 | Maiorino et al. |
| 2010/0256677 A1 | 10/2010 | Albertorio et al. |
| 2010/0268273 A1 | 10/2010 | Albertorio et al. |
| 2011/0022083 A1* | 1/2011 | DiMatteo ........... A61B 17/0401 606/228 |
| 2011/0270278 A1* | 11/2011 | Overes ............... A61B 17/0057 606/228 |
| 2012/0004669 A1 | 1/2012 | Overes et al. |
| 2012/0065732 A1 | 3/2012 | Roller et al. |
| 2012/0109156 A1 | 5/2012 | Overes et al. |
| 2012/0143215 A1 | 6/2012 | Corrao et al. |
| 2012/0150223 A1 | 6/2012 | Manos et al. |
| 2013/0072972 A1 | 3/2013 | Maiorino |
| 2013/0072973 A1 | 3/2013 | Maiorino et al. |
| 2013/0079822 A1 | 3/2013 | Maiorino et al. |
| 2013/0110165 A1* | 5/2013 | Burkhart ........... A61B 17/0401 606/232 |
| 2013/0268073 A1 | 10/2013 | Albertorio et al. |
| 2013/0296934 A1* | 11/2013 | Sengun ................. A61B 90/92 606/232 |
| 2013/0296937 A1 | 11/2013 | Dreyfuss et al. |
| 2014/0081399 A1 | 3/2014 | Roller et al. |
| 2014/0121701 A1 | 5/2014 | Dreyfuss et al. |
| 2014/0128915 A1 | 5/2014 | Dreyfuss et al. |
| 2014/0277133 A1* | 9/2014 | Foerster ............ A61B 17/0401 606/232 |
| 2014/0364909 A1 | 12/2014 | Dreyfuss et al. |
| 2015/0005819 A1 | 1/2015 | Dreyfuss et al. |
| 2015/0342596 A1 | 12/2015 | Dreyfuss et al. |
| 2016/0007989 A1 | 1/2016 | Overes et al. |
| 2016/0270777 A1 | 9/2016 | Miller et al. |
| 2016/0354078 A1 | 12/2016 | Overes et al. |
| 2016/0354197 A1 | 12/2016 | Roller et al. |
| 2017/0143328 A1 | 5/2017 | Overes et al. |
| 2017/0164940 A1 | 6/2017 | Dreyfuss et al. |
| 2017/0231618 A1 | 8/2017 | Dreyfuss et al. |
| 2017/0252147 A1 | 9/2017 | Albertorio et al. |
| 2017/0296328 A1 | 10/2017 | Albertorio et al. |
| 2017/0333026 A1 | 11/2017 | Dreyfuss et al. |
| 2017/0360420 A1 | 12/2017 | Corrao et al. |
| 2018/0344447 A1 | 12/2018 | Albertorio et al. |
| 2019/0070007 A1* | 3/2019 | Bettenga ........... A61B 17/0401 |
| 2019/0201185 A1 | 7/2019 | Albertorio et al. |
| 2020/0178947 A1 | 6/2020 | Corrao et al. |

FOREIGN PATENT DOCUMENTS

| | | |
|---|---|---|
| KR | 10-2008-0055815 A | 6/2008 |
| KR | 10-2013-0067196 A | 6/2013 |
| KR | 10-2013-0092425 A | 8/2013 |
| KR | 10-1626083 B1 | 5/2016 |
| KR | 10-2016-0087580 A | 7/2016 |

* cited by examiner

METHOD OF PREPARING SUTURE ANCHOR USING SUTURE AND PREPARED SUTURE ANCHOR

CROSS REFERENCE TO RELATED APPLICATIONS

This application is a National Stage Patent Application of PCT International Patent Application No. PCT/KR2019/005111 (filed on Apr. 27, 2019) under 35 U.S.C. § 371, which claims priority to Korean Patent Application No. 10-2018-0061558 (filed on May 30, 2018), the teachings of which are incorporated herein in their entireties by reference.

TECHNICAL FIELD

The present invention relates to a method of preparing a suture anchor using a suture and a prepared suture anchor and, more particularly, to a method of preparing a suture anchor capable of attaching a soft tissue such as a damaged joint membrane, a cartilage, a muscle, or a ligament to a bone by sewing, and to a suture anchor with a special structure prepared by the method.

BACKGROUND ART

Generally, for the rapid healing of patients, the introduction and development of minimal invasive surgery or robotic surgery in the orthopedic field is a fact of life in the medical world.

In the orthopedic field, a current trend is to apply arthroscopic surgery to ligament damage or muscle tears due to sports injuries, arthritis, or degenerative diseases, and the trend is expected to continue in the future.

Accordingly, a suture anchor is used to attach a soft tissue such as a damaged joint membrane, a cartilage, a muscle, or a ligament to a bone.

The surgical proceeds by performing mini-incision on a lesion portion or fixing a lesion muscle or ligament with a suture (for example, a fiber wire suture) after checking the lesion portion with arthroscopy, and inserting a screw (anchor) on a thread into the exposed lesion portion.

The anchor is provided with a suture so that a detached ligament or muscle can be reattached to a bone by being sewn and being pulled.

When a recovery size (area) of a damaged portion is large, a plurality of anchors is needed to properly attach a damaged joint membrane, a cartilage, a muscle, or a ligament to a bone.

However, as disclosed in Korean Patent Application Publication No. 10-2013-0067196, Korean Patent Application Publication No. 10-2008-0055815, and Korean Patent No. 10-1626083, most conventional anchors are made of metallic materials or absorbable or non-absorbable polymer materials. Accordingly, the number and positions of anchoring points may be restricted due to a size of the plurality of anchors and the use of the plurality of anchors may cause a significant impact on recovery of a bone.

However, when reducing the number of anchors or using a plurality of mini anchors, there is a problem that it is difficult to supply and maintain fixation strength.

DOCUMENTS OF RELATED ART (Patent Document 1) Korean Patent Application Publication No. 10-2013-0067196 A;

(Patent Document 2) Korean Patent Application Publication No. 10-2008-0055815 A;

(Patent Document 3) Korean Patent No. 10-1626083 B1.

DISCLOSURE

Technical Problem

Accordingly, the present invention has been made keeping in mind the above problems occurring in the prior art, and the present invention provides a method of preparing a suture anchor using a suture in a special way and a suture anchor having a special structure prepared by the method. The special way used in the method is configured such that a suture being biological compatibility biologically compatible use in a human body is knitted in the special way to form a plurality of knots, the plurality of knots is cut at a predetermined length to form a knitting member having a predetermined width and the predetermined length, and another suture capable of attaching a soft tissue such as a damaged joint membrane, a cartilage, a muscle, or a ligament to a bone by sewing is provided in the knitting member in a longitudinal direction of the knitting member.

Thus, reliability of the suture anchor of the present invention is improved by using materials with biological compatibility.

In addition, when a recovery size (area) of a damaged portion is large, a surgery using the suture anchor of the present invention does not require the use of a plurality of anchors for providing an appropriate fixation strength and properly attaching the soft tissue such as the damaged joint membrane, the cartilage, the muscle, or the ligament to a bone, so that the surgery for bone recovery can be performed easily and quickly without affecting the soft tissue and the bone.

Technical Solution

In order to accomplish the above object, the present invention provides a suture anchor using a suture, the suture anchor is prepared as follows. First, two rows of first sutures constituting a pair with biological compatibility with a human body are knitted to continuously form a plurality of knots, and the knitted sutures are cut to a predetermined length to form a knitting member.

Next, a plurality number of second sutures that attach a soft tissue such as a damaged joint membrane, a cartilage, a muscle, or a ligament to a bone by sewing may be provided between one knot and another knot of knots in a longitudinal direction of the knitting member by sewing in a long line.

Meanwhile, a method of preparing the suture anchor using a suture may include: a first step (A) of bending the pair of first sutures having biological compatibility on the human body into a "U"-shape;

a second step (B) of, after the first step (A), crossing a first end and a second end of the pair of first sutures bent into the "U"-shape into an "X"-shape to form an open space portion at a front portion and a loop space portion at a rear portion;

a third step (C) of, after the second step (B), using a separate knitting tool, passing the tool through the loop space portion and then putting the tool into the open space portion from a lower side of the "X"-shape to hook the first end, pulling the tool rearwards, and further pulling rearwards the tool being in a state of passing through the loop space portion to form a knot;

a fourth step (D) of, after the knot is formed by performing the third step (C), repeating the third step (C) several times to form a plurality of knots in the predetermined length by continuing rearward from the previous knot, a fifth step (E) of, after the fourth step (D), cutting the knitted first sutures as the predetermined length and bonding the cut portion at the same time so that the cut portion is not untied, thereby forming a plurality of knitting members having the predetermined length; and a sixth step (F) of, after the fifth step (E), sewing a predetermined number of second sutures that attach the soft tissue such as the damaged joint membrane, the cartilage, the muscle, or the ligament to the bone by sewing between one knot and another knot of the knots in the longitudinal direction of the plurality of knitting members having the predetermined length.

Advantageous Effects

As described above, the suture anchor according to the embodiment of the present invention is prepared as follows. A suture having biological compatibility for use in the human body is knitted in a special way, the knitted suture is cut at a predetermined length to form a knitting member having a predetermined width and the predetermined length, and another suture capable of attaching soft tissue such as a damaged joint membrane, a cartilage, a muscle, or a ligament to a bone by sewing is provided in the knitting member along a longitudinal direction of the knitting member.

According to the embodiment of the present invention, the knitting member is easily deformed from a long rod shape to a lump shape, so that the suture anchor can be firmly fixed to a hole of the bone so as not to be removed therefrom, and can have a relatively large fixation strength when the soft tissue is pulled during sewing.

Meanwhile, according to the embodiment of the present invention, the suture anchor uses a material with biological compatibility, thereby being increased in compatibility. In addition, when the recovery size (area) of a damaged portion is large, the surgery using the suture anchor of the present invention does not require the use of a plurality of anchors for providing appropriate fixation strength and properly attaching the soft tissue such as the damaged joint membrane, the cartilage, the muscle, or the ligament to a bone, so that the surgery can be performed easily and quickly.

Meanwhile, most conventional anchors are made of metallic materials or absorbable or non-absorbable polymer materials, thus the number and position of anchoring points may be restricted due to the size of a plurality of anchors. However, the use of the suture anchor of the present invention has few restrictions on the number and position of the anchoring points, and does not require perforating a plurality of holes in a bone unlike the conventional anchors, so that tissue recovery can be performed quickly without affecting the soft tissue and the bone.

DESCRIPTION OF DRAWINGS

FIGS. 1A to 1F are views showing a preparation method of a knitting member of the present invention, in which:

FIG. 1A is a view showing a first suture configured as two rows of sutures and bent in a "U"-shape;

FIG. 1B is a view showing the first sutures that are crossed in an "X"-shape;

FIG. 1C is a view showing a state before a first knot is formed using the first sutures;

FIG. 1D is a view showing a state after the first knot is formed using the first sutures;

FIG. 1E is a view showing a plurality of knots formed in a long shape using the first sutures; and FIG. 1F is a view showing the knitting member at the rear, the knitting member being formed by cutting the knots at a predetermined length.

FIGS. 2A to 2C are views showing coupling states of a suture anchor according to an embodiment of the present invention and an anchor inserting device, in which:

FIG. 2A is a view showing a configuration of the suture anchor according to the embodiment of the present invention;

FIG. 2B is a view showing a state in which the suture anchor according to the embodiment of the present invention is coupled to the anchor inserting device; and FIG. 2C is an enlarged view showing a main coupling portion of the suture anchor and the anchor inserting device.

FIGS. 3A to 3C are views showing a method of using the suture anchor of the present invention, in which:

FIG. 3A is a view showing the suture anchor that is located close to a hole of a bone;

FIG. 3B is a view showing the suture anchor that is inserted deep into the bone through the hole of the bone; and FIG. 3C is a view showing the suture anchor in the bone, the suture anchor being deformed into a lump shape by pulling.

DESCRIPTION OF REFERENCE NUMERALS

Figure 1A:
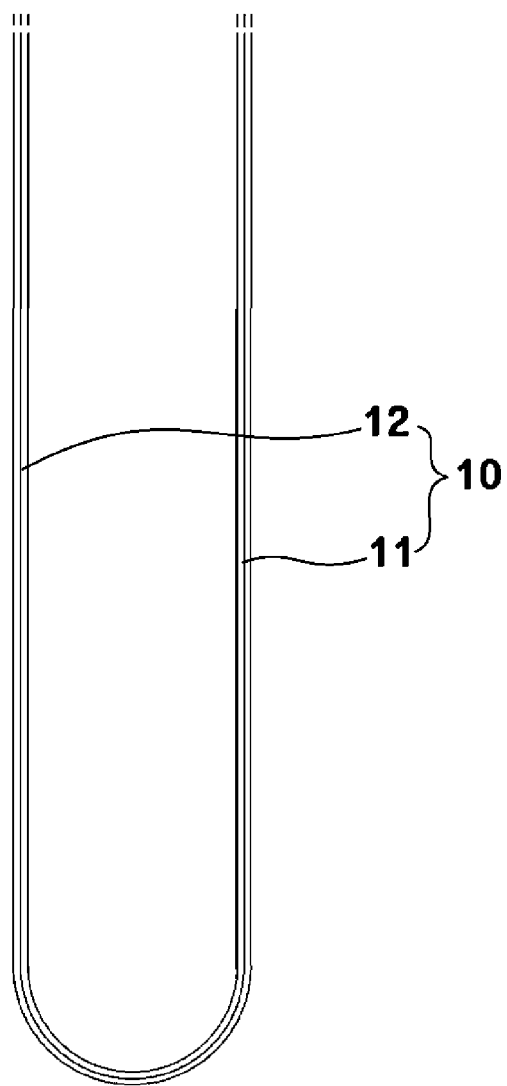

| a: loop space portion | b: open space portion |
|---|---|
| 1: bone | 1a: hole |
| 10: first suture | 10a: knot |
| 11: first end | 12: second end |
| 20: second suture | 100: knitted member |
| 200: anchor inserting device | |

BEST MODE

Hereinafter, an embodiment of the present invention will be described in detail with reference to FIGS. 1A to 3C. The embodiment described below will be described to help provide more comprehensive understanding of the present invention, and those skilled in the art will appreciate that the present invention can be embodied in many alternate forms different from the embodiment of the present invention. In the following description, a detailed description of known functions and components incorporated herein will be omitted when it may make the subject matter of the present invention unclear. In addition, the shapes, sizes, etc. of components in the accompanying drawings may be exaggerated to make the description clearer.

The present invention relates to a method of preparing a suture anchor using a suture in a special preparation way and to a suture anchor with a special structure prepared by the method. First, a first biologically compatibility suture 10 that has been widely used in the human body is knitted in the special way to form a plurality of knots 10a. Next, the knitted suture is cut at a predetermined length to form a knitting member 100 having a predetermined width and the predetermined length. Finally, a second suture 20 is provided between one knot 10a of the plurality of knots and another knot 10a thereof by sewing in a longitudinal direction of the knitting member 100, the second suture 20 being capable of attaching a soft tissue such as a damaged joint membrane, a cartilage, a muscle, or a ligament to a bone by sewing.

The embodiment of the present invention for the method of preparing the suture anchor using a suture will be described.

According to the embodiment of the present invention, the method of preparing the suture anchor using a suture is configured such that the first suture 10 having biological compatibility for use in the human body is provided as two rows of sutures constituting a pair, and the first sutures 10 are bent in a "U"-shape, as shown in FIG. 1A.

Figure 1B:
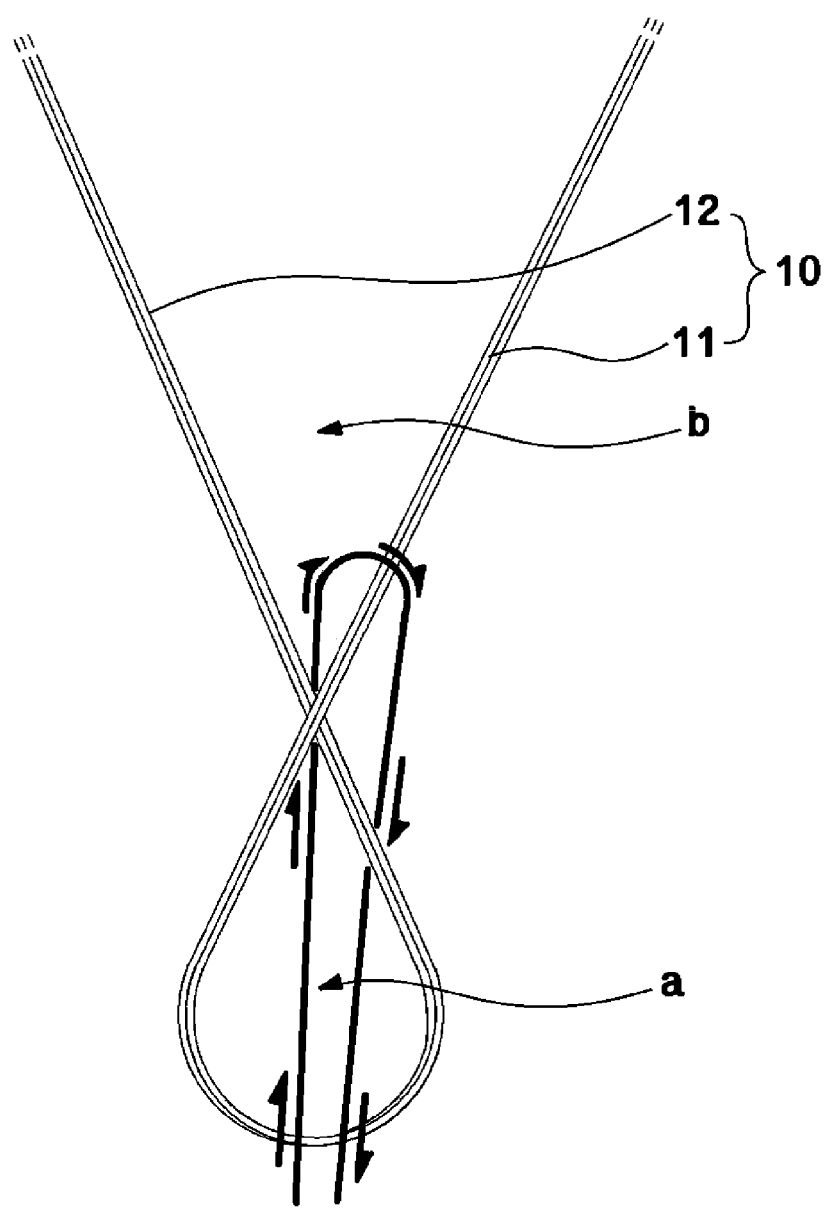
Figure 1C:
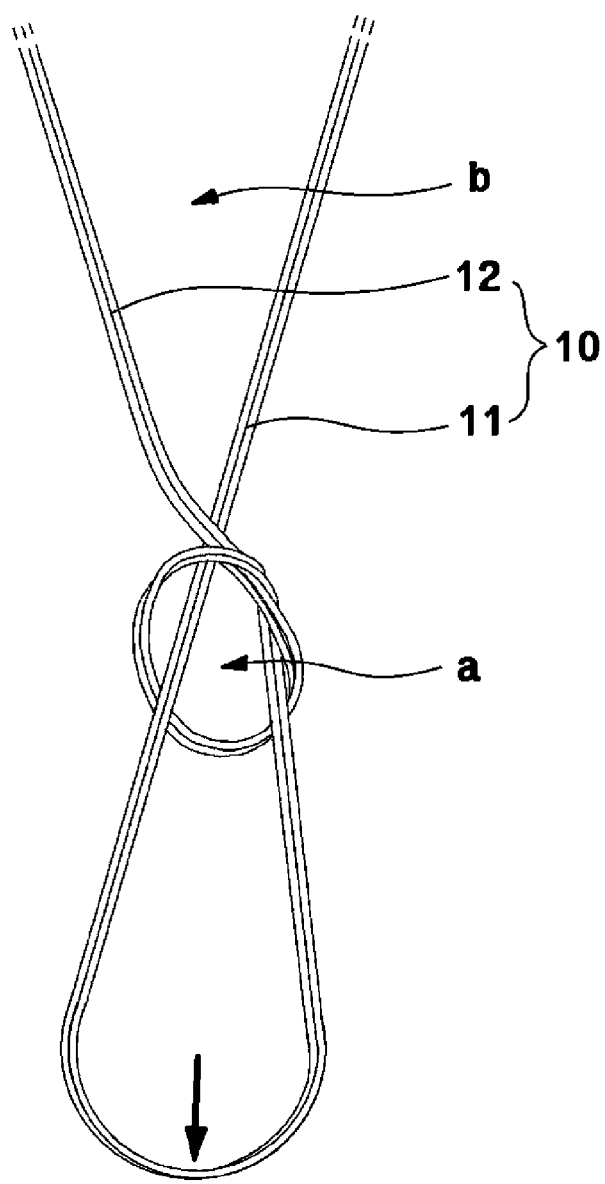
Figure 1D:
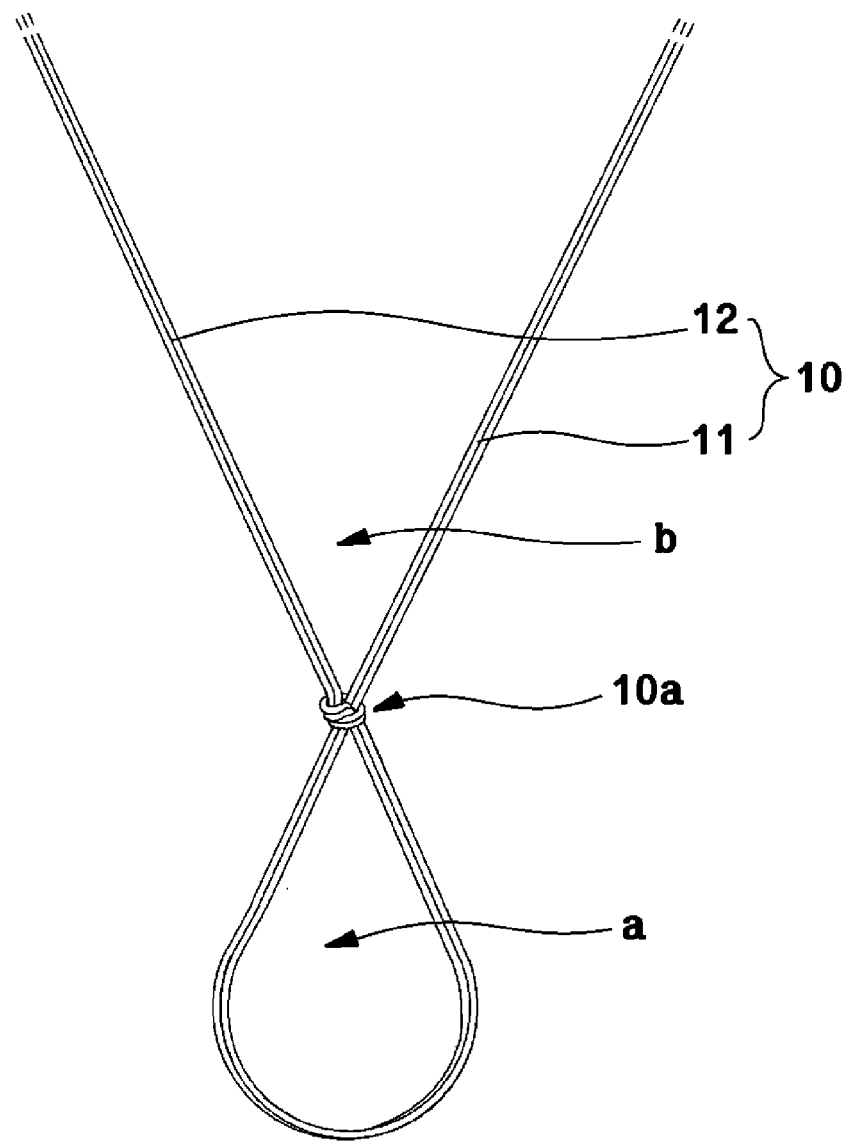

An open space portion b is formed at the front of the "U"-shape and a loop space portion a connected thereto is formed at the rear thereof by crossing a first end 11 of the pair of the first sutures 10 and a second end 12 thereof into an "X"-shape, as shown in FIG. 1B. Then, using a tool such as a finger or a knitting needle, the first end 11 is pulled out rearwards by passing the tool through the loop space portion a and inserting the tool into a lower side of the open space portion b from a lower side of the "X"-shape to hook a portion of the first end 11 as shown in FIG. 1C. As shown in FIG. 1D, a first knot 10a is formed by further pulling the hooked portion of the first end 11 rearwards, in a state of passing through the inside of the loop space portion a as shown in FIG. 1C.

Figure 1E:
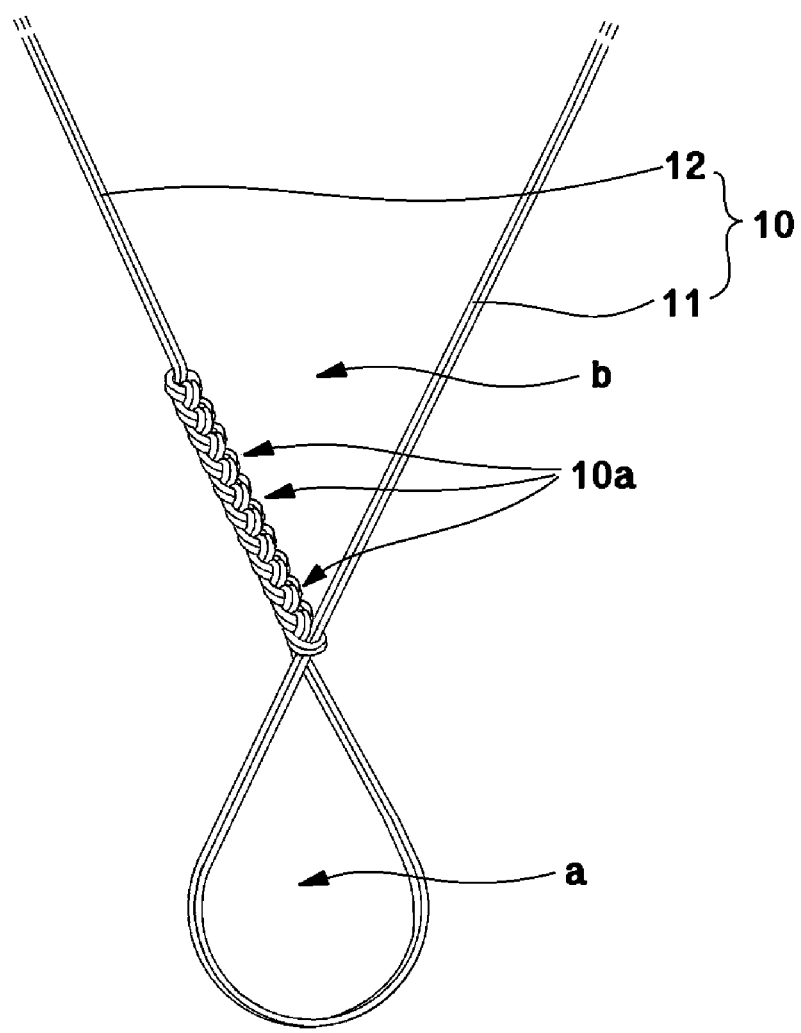
Figure 1F:
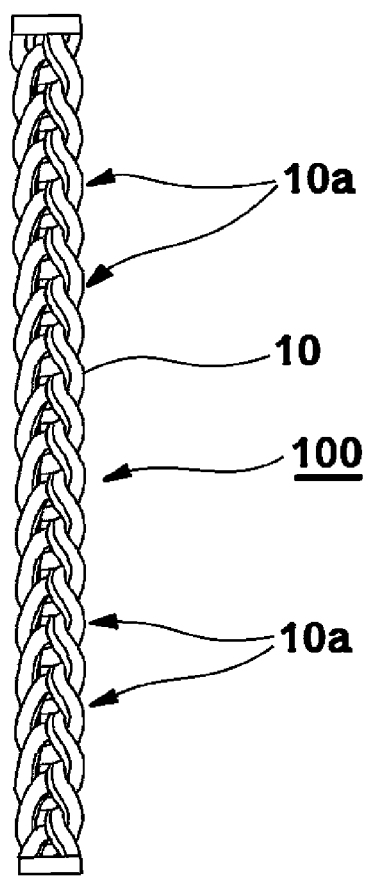

After the knot 10a is formed as FIG. 1D, the plurality of knots 10a is formed in a long line as shown in FIG. 1E by repeating several times the process of forming the knot 10a. The process is configured by passing the tool such as the finger or the knitting needle through the loop space portion a, inserting the tool from the lower side of the "X"-shape into the lower side of the open space portion b to hook the first end 11, and passing again the hooked portion of the first end 11 through the inside of the loop space portion a and further pulling the portion. Then, the knitting member 100 having the predetermined length is formed by cutting the plurality of knots at the predetermined length and by bonding the cut portion so that the cut portion is not untied, as shown in FIG. 1F.

Figure 2A:
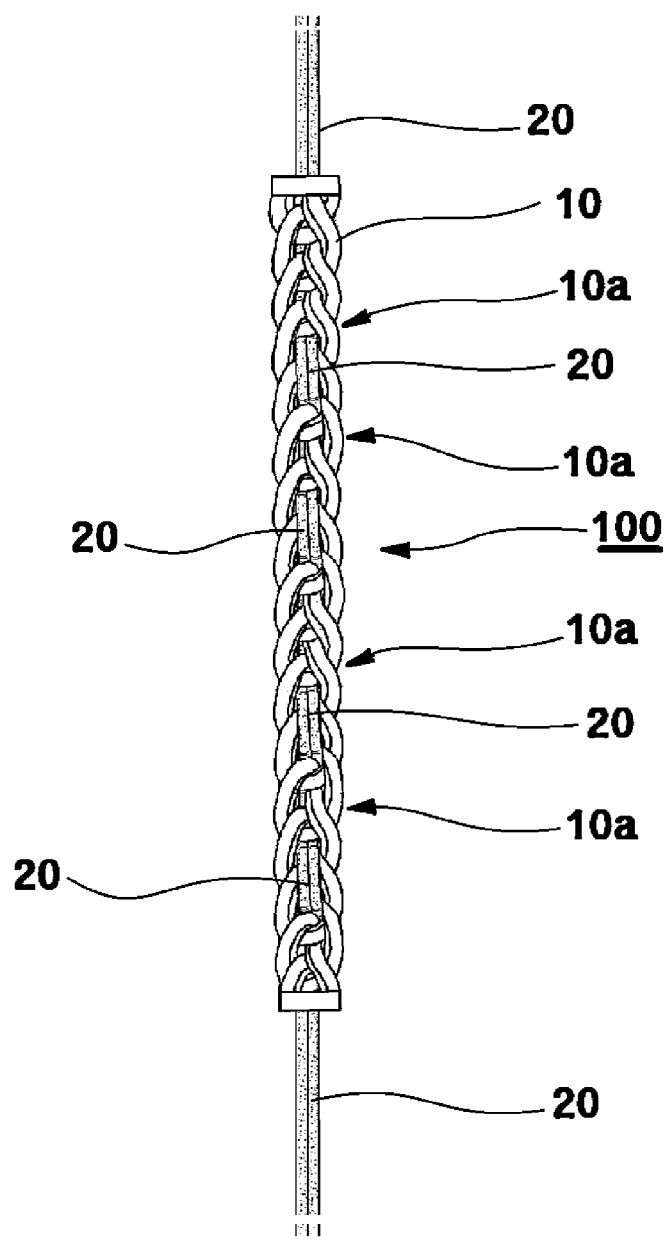

After the knitting member 100 is formed, as shown in FIG. 2A, a predetermined number of second sutures 20 are provided between one knot 10a and the other knot 10a of the knots by sewing in the longitudinal direction of the knitting member 100, the second suture 20 being capable of attaching the soft tissue such as the damaged joint membrane, the cartilage, the muscle, or the ligament to the bone by sewing.

According to the present invention, the suture anchor prepared by the method uses the suture having biological compatibility for use in the human body, so that the suture anchor of the present invention has excellent compatibility. In addition, the knitting member is cut to have a predetermined width and a predetermined length and the cut portion is bonded at the same time, so that the cut portion is not untied.

The predetermined number of second sutures 20 capable of attaching the soft tissue such as the damaged joint membrane, the cartilage, the muscle, or the ligament to the bone by sewing is provided between one knot 10a and the other knot 10a of the knots by sewing in longitudinal the direction of the knitting member 100. Thus, unlike most conventional anchors, that is, anchors made of metallic materials, or absorbable or non-absorbable polymer materials, the suture anchor of the present invention is provided with the special structure configured to deform a shape of the knitting member 100.

Hereinafter, a method of using the suture anchor of the present invention will be described.

Figure 2B:
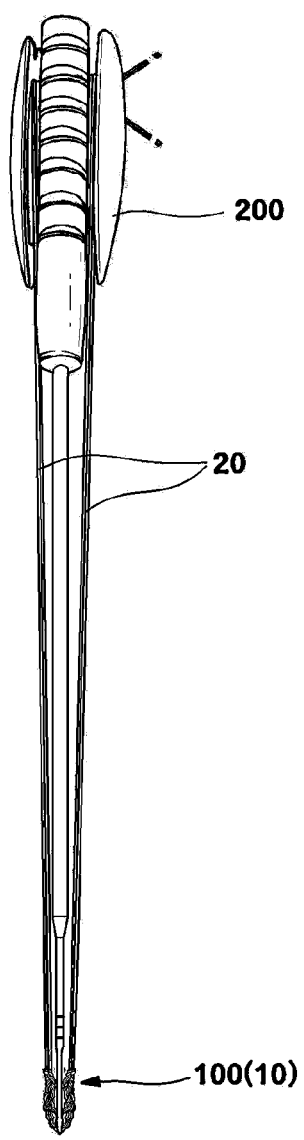
Figure 2C:
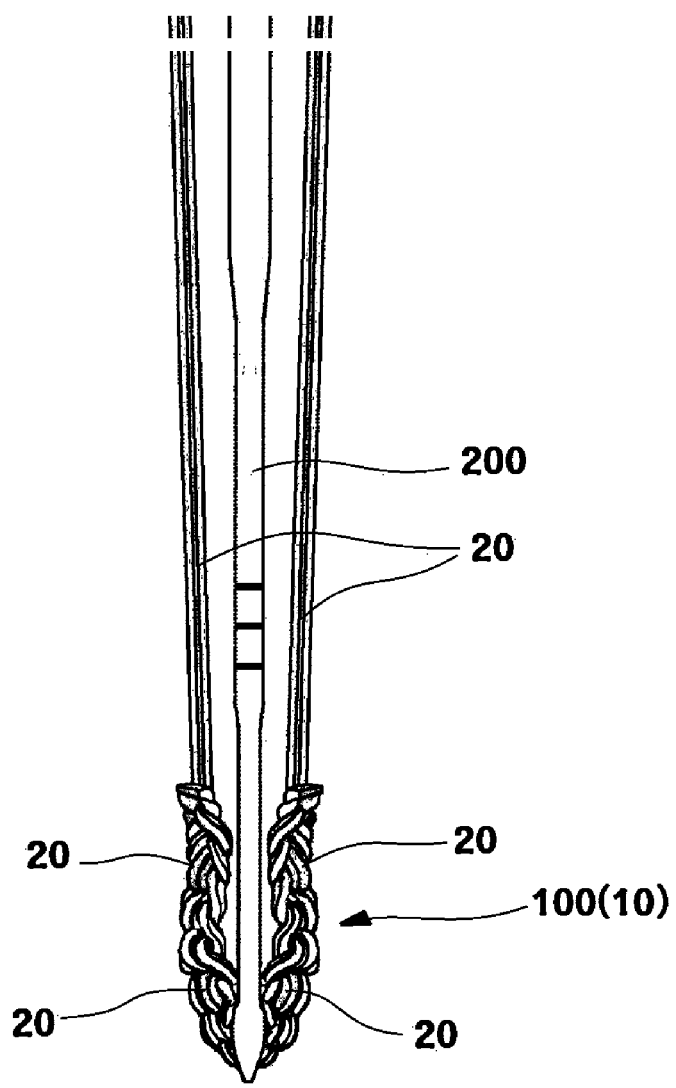
Figure 3A:
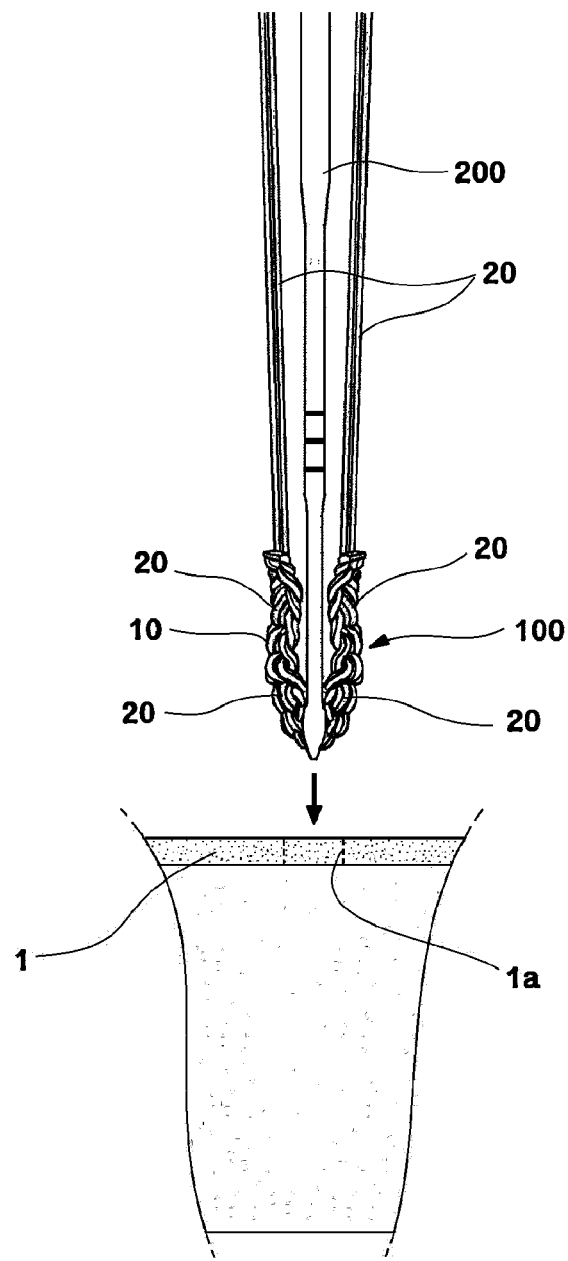

In order to use the suture anchor according to the embodiment of the present invention, first, on a portion to be operated, a hole 1a is bored on a bone 1 using a boring device (not shown) as shown in FIGS. 2B to 2C. Next, a middle portion of the knitting member 100 making the suture anchor is put in a groove provided in a front end of an anchor inserting device 200, and to make easy insertion of the knitting member 100, the knitting member 100 in a bent state of the "U"-shape is positioned above the hole 1a provided in the bone 1, as shown in FIG. 3A.

Figure 3B:
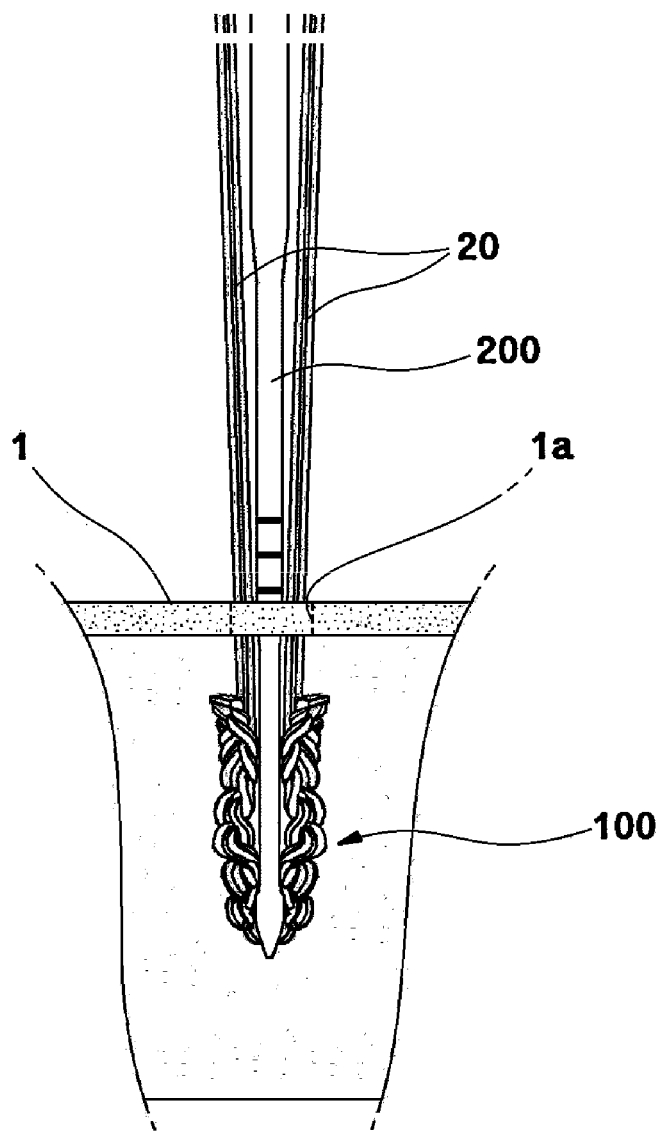

Then, the knitting member 100 is inserted deep into the bone 1 through the hole 1a of the bone 1, as shown in FIG. 3B.

Figure 3C:
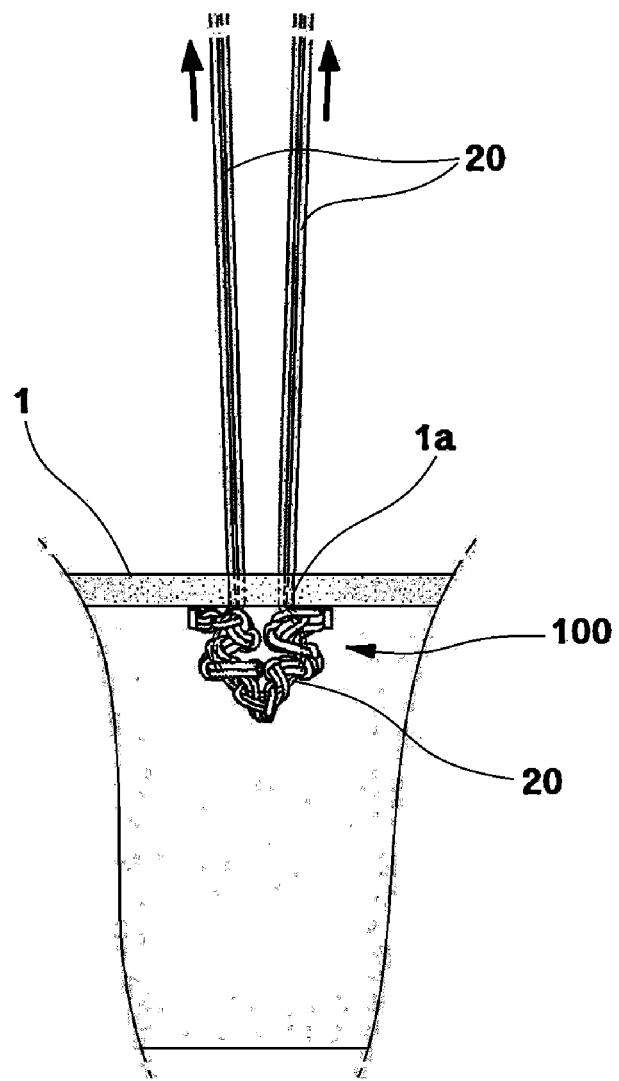

In the state of FIG. 3B, the groove provided in the front end of the anchor inserting device 200 is pulled back. More preferably, as shown in FIG. 3C, after closing an opening of the hole 1a of the bone 1, opposite ends of the second sutures 20 are pulled rearwards, the second sutures being connected to the knitting member 100 by sewing the predetermined number of the second sutures in the longitudinal direction of the knitting member 100. Then, as the opposite ends of the knitting member 100 are compressed, the entire knitting member 100 is gradually deformed from a long rod shape into a lump shape, and a volume of the lump is increased more than a diameter of the hole 1a of the bone 1, so that the knitting member 100 deformed into the lump shape cannot be removed from the hole 1a of the bone 1 even when the second sutures 20 are pulled rearwards.

Accordingly, the second sutures 20 are used to sew the soft tissue such as the damaged joint membrane, the cartilage, the muscle, or the ligament to the bone, and are pulled with a predetermined strength to attach the tissue close to the bone 1.

The suture anchor according to the embodiment of the present invention is prepared in the following special way: the first sutures 10 having biological compatibility for use in the human body are knitted in the special way to form the plurality of knots 10a; the plurality of knots 10a is cut at the predetermined length to form the knitting member 100 having the predetermined width and length; and the other sutures that can attach the soft tissue such as the damaged joint membrane, the cartilage, the muscle, or the ligament to the bone by sewing, that is, the second sutures 20, are provided between the knots in the longitudinal direction of the knitting member 100. In addition, the knitting member 100 is deformed from the long rod shape into the lump shape, so that the suture anchor of the present invention is firmly fixed in the hole 1a of the bone 1 so that it is not removed therefrom, and has relatively large fixation strength when the soft tissue is pulled during sewing.

Accordingly, when a recovery size (area) of a damaged portion is large, a surgery using the suture anchor of the present invention does not require the use of a plurality of anchors that provides appropriate fixation strength needed to proper attach the soft tissue such as the damaged joint membrane, the cartilage, the muscle, or the ligament to the bone 1, so that the surgery can be performed easily and quickly.

In addition, when the recovery size (area) of the damaged portion is large, conventionally, since most anchors are anchors made of the metallic materials, or the absorbable or non-absorbable polymer materials, the number and positions of anchoring points may be restricted due to a size of the plurality of anchors. However, the use of the suture anchor of the present invention has few restrictions on the number and positions of the anchoring points.

In addition, according to the present invention, it is unnecessary to perforate a plurality of holes 1a in the bone 1 in comparison with the related art, so that tissue recovery can be performed quickly without affecting the soft tissue and the bone.

INDUSTRIAL APPLICABILITY

According to the embodiment of the present invention, the suture anchor using a suture can be used for suturing a soft tissue such as a damaged joint membrane, a cartilage, a muscle, a ligament, or the like.

The invention claimed is:

1. A suture having a suture anchor, comprising:
   biologically compatible first sutures configured as rows of sutures constituting a pair and knitted to continuously form a plurality of knitted knots, wherein the knitted knots are cut and bonded to a predetermined length to form a knitting member having a predetermined width and a predetermined length; and
   at least one second suture configured to attach to a soft tissue for sewing provided between each of the plurality of the knitted knots in a longitudinal direction of the knitting member by sewing in a long line.

2. The suture of claim 1, wherein when the knitting member is inserted into an anatomical location and when the at least one second suture is pulled rearwards, the knitting member is deformed from a long rod shape to a lump shape and is increased in diameter to be larger than a diameter of the anatomical location.

3. The suture of claim 1, wherein the at least one second suture attaches to a damaged joint membrane, a cartilage, a muscle, or a ligament.

* * * * *